(12) United States Patent
Sampayan et al.

(10) Patent No.: US 11,913,675 B2
(45) Date of Patent: Feb. 27, 2024

(54) DISINFECTION SYSTEM WITH HIGH THROUGHPUT AND LOW POWER REQUIREMENTS

(71) Applicants: Lawrence Livermore National Security, LLC, Livermore, CA (US); Opcondys, Inc., Manteca, CA (US)

(72) Inventors: Stephen Sampayan, Manteca, CA (US); Kristin Cortella Sampayan, Manteca, CA (US)

(73) Assignees: Lawrence Livermore National Security, LLC, Livermore, CA (US); Opcondys, Inc., Manteca, CA (US)

( * ) Notice: Subject to any disclaimer, the term of this patent is extended or adjusted under 35 U.S.C. 154(b) by 274 days.

(21) Appl. No.: 17/327,556

(22) Filed: May 21, 2021

(65) Prior Publication Data

US 2021/0364177 A1    Nov. 25, 2021

Related U.S. Application Data

(60) Provisional application No. 63/029,441, filed on May 23, 2020.

(51) Int. Cl.
  *F24F 8/80* (2021.01)
  *F24F 8/192* (2021.01)
  *F24F 11/88* (2018.01)

(52) U.S. Cl.
  CPC .............. *F24F 8/194* (2021.01); *F24F 8/80* (2021.01); *F24F 11/88* (2018.01)

(58) Field of Classification Search
  CPC .............. F24F 8/194; F24F 8/80; F24F 11/88
  See application file for complete search history.

(56) References Cited

U.S. PATENT DOCUMENTS

| 9,142,339 B2 | 9/2015 | Sampayan |
| 9,748,859 B2 | 8/2017 | Sampayan |
| 10,333,010 B2 | 6/2019 | Sampayan |

FOREIGN PATENT DOCUMENTS

JP    S60227851 A  * 11/1985

OTHER PUBLICATIONS

Akiyama, Hidenori, et al., "Bioelectrics", Springer, Japan, 2017.
American Society of Heating, Refrigerating and Air-Conditioning Engineers (ASHRAE), "Emerging Issue Reports: Pandemic SARS-CoV-2 and Airborne Transmission Emerging Issue Brief," Apr. 17, 2020.
Beroz, J., et al., "Stability limit of electrified droplets," Phys. Rev. Let. 122, 244501, 2019.

(Continued)

*Primary Examiner* — Robert A Hopkins
(74) *Attorney, Agent, or Firm* — Perkins Coie LLP

(57) ABSTRACT

Devices, methods and techniques are disclosed to perform high confidence sterilization of indoor air with low power requirements. In one example aspect, a sterilization device includes a power source, an energy storage coupled to the power source and configured to store electric charges, a set of electrodes arranged in a specified geometry to have a fixed characteristic impedance, and a switch positioned between the energy storage and the set of electrodes. The switch is configured to operate to establish a pulsed electric field on the set of electrodes.

30 Claims, 13 Drawing Sheets

(56) References Cited

OTHER PUBLICATIONS

Checa, Marti, et al., , "Mapping the dielectric constant of a single bacterial cell at the nanoscale with scanning dielectric force volume microscopy," Nanoscale, vol. 11, pp. 20809-20819, Oct. 2019.

Cuervo, Ana, et al., "Direct measurement of the dielectric polarization properties of DNA," Proc. Natl. Acad. Sci. USA, v. 111, No. 35, pp. E3624-E3630, Sep. 2014.

Eliasson, Baldur, et al., "Modeling and applications of silent discharge plasmas," IEEE Trans. Plas. Sci., v. 19, No. 2, pp. 309-323, Apr. 1991.

Fumagalli, Laura, et al., "Label-free identification of single dielectric nanoparticles and viruses with ultraweak polarization forces," Nat. Mater. V. 11, No. 9, 808-816, 2012.

Gallagher, Michael J., et al., , "Rapid inactivation of airborne bacteria using atmospheric pressure dielectric barrier grating discharge," IEEE Trans. Plas. Sci., v. 35, No. 5, pp. 1501-1510, Oct. 2007.

Guo, Zhen-Dong, et al., "Aerosol and surface distribution of severe acute respiratory syndrome coronavirus 2 in hospital wards, Wuhan, China, 2020". Emerg Infect Dis. Jul. 2020.

Hall, E. H., et al., "Nanosecond pulsed electric fields have differential effects on cells in the S-Phase," DNA Cell Biol. V. 26, pp. 160-171, 2007.

Huang, R., et al., "Removal of viable bioaerosol particles with a low-efficiency HVAC filter enhanced by continuous emission of unipolar air ions," Indoor Air. V. 18, No. 2, pp. 106-112, Apr. 2008.

Majewski, Jacek, "Measurement methods for size and charge distributions of electrosprayed water droplets," J. Przegląd Elektrotechniczny, v. R90, No. 4, pp. 177-180, 2014.

Majewski, Jacek, "Measurement techniques concerning droplet size distribution of electrosprayed water," J. Przegląd Elektrotechniczny, v. R89, No. 3b, pp. 300-302, 2013.

McDevitt, James J., et al., "Aerosol susceptibility of influenza virus to UVC light," Appl. Envir. Microbiology, v. 78, No. 6, pp. 1666-1669, Jan. 2012.

Mizuno, Akira, et al., "Inactivation of viruses using pulsed high electric fields," in the Conference Record of the 1990 IEEE Industry Applications Society Annual Meeting, Seattle, WA, pp. 713-719, Oct. 7-12, 1990.

Orriere, Thomas, et al., "Ionization and recombination in nano second repetitively pulsed microplasmas in air at atmospheric pressure," J. Phy. D: Appl. Phy., v. 51, No. 49 494002, 2018.

O'Shaughnessy, Ben, et al., "Manning-Oosawa Counterion Condensation," Phys. Rev. Lett. V. 94, pp. 048302, Feb. 2005.

Pastuszka, Jozef S., et al., "The Study of the Sterilization of the Indoor Air in Hospital/Clinic Rooms by Using the Electron Wind Generator," Int. J. Environ. Res. Public Health, v. 16, No. 24, pp. 4935-4946, Dec. 5, 2019.

Rayleigh, Lord, "On the equilibrium of liquid conducting masses charged with electricity," Phil. Mag. v. 14, pp. 184-186, 1882.

Sampayan, K., et al., "Wide bandgap photoconductive switches driven by laser diodes as a high-voltage MOSFET replacement for bioelectrics and accelerator applications, " 2019 IEEE Pulsed Power & Plasma Science (PPPS), Orlando, FL, USA, 2019, pp. 1-4.

Schoen, Lawrence J., et al., "Guidance for building operations during the COVID-19 pandemic," ASHRAE Journal Newsletter, Mar. 24, 202.

Taylor, Sir Geoffrey, "Disintegration of water drops in an electric field," Proc. R. Soc. Lond. V. A280, pp. 383-397, 1964.

Vaze, Nachiket D., et al., "Inactivation of bacteria in flight by direct exposure to nonthermal plasma," IEEE Trans. Plas. Sci., v. 38, No. 11, pp. 3234-3240, Nov. 2010.

Yao, Maosheng, et al., "Inactivation of microorganisms using electrostatic fields," Envi. Sci. & Tech., v. 39, No. 9, pp. 3338-3344, 2005.

Zhou, Chunda, et al., "Collapse of DNA under alternating electric fields," Phy. Rev. E, Stat. Nonlin. Soft Matter Phy., v. 92, No. 1, 012714, Jul. 2015.

Zimmerman, U., et al., "Biophysics of electroinjection and electrofusion," J. of Electrostatics, 21, pp. 209-345, 1988.

\* cited by examiner

400

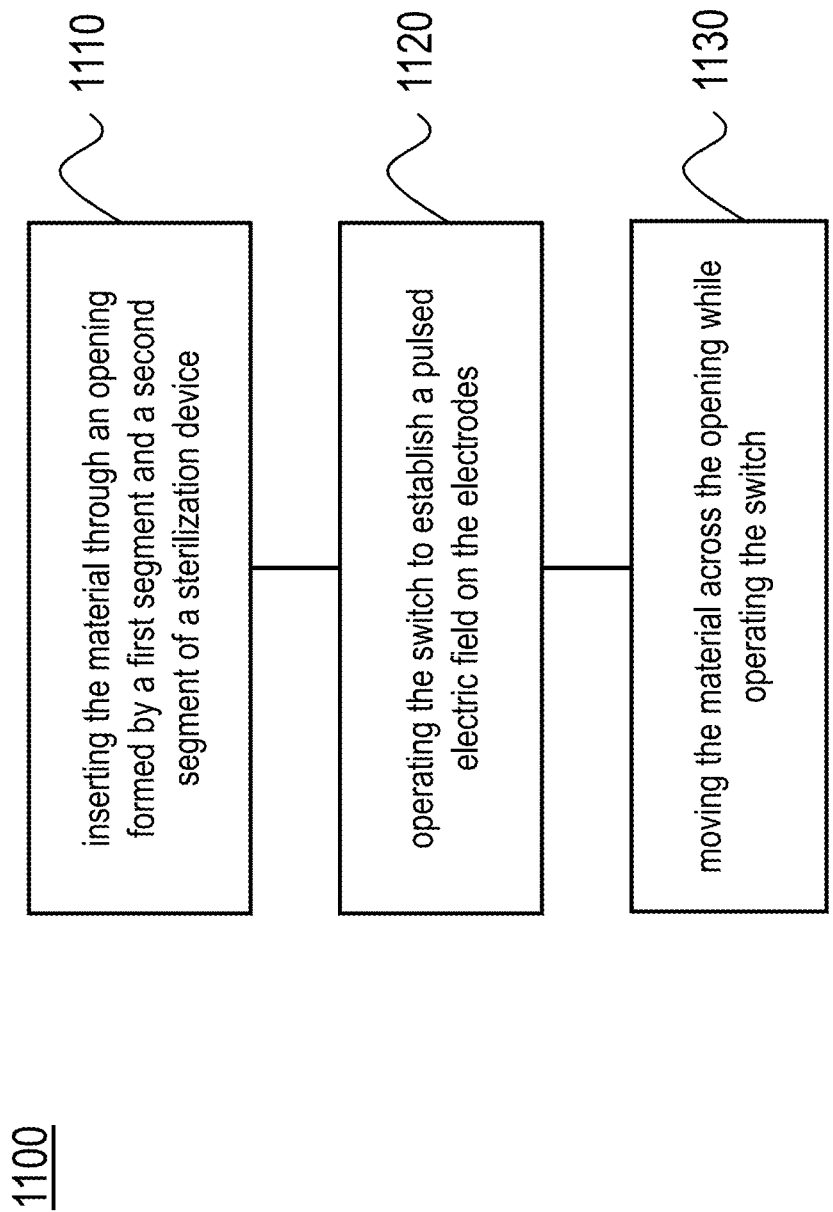

DISINFECTION SYSTEM WITH HIGH THROUGHPUT AND LOW POWER REQUIREMENTS

CROSS REFERENCE TO RELATED APPLICATIONS

This patent document claims priority to and benefits of U.S. Provisional Patent Application No. 63/029,441 entitled "High throughput, high confidence, low power requirement, disinfection system" and filed May 23, 2020. The entire contents of the before-mentioned patent application are incorporated by reference as part of the disclosure of this patent document.

STATEMENT REGARDING FEDERALLY SPONSORED RESEARCH

This invention was made with Government support under Contract No. DE-AC52-07NA27344 awarded by the United States Department of Energy. The Government has certain rights in the invention.

TECHNICAL FIELD

This document generally relates to sterilization and disinfection systems using high voltage pulses.

BACKGROUND

The COVID-19 disease was declared as a pandemic by the World Health Organization in March 2020 because of its rapid worldwide spread: approximately 160 million cases and over 3 million deaths have been reported as of May 2021. The virus responsible for this disease is the SARS-CoV-2, which is part of the family of Coronaviruses that affects the respiratory system with mild to moderate symptoms, and sometimes fatal complications. It is mainly spread by persons in close contact through aerosols created by breathing, coughing, and/or sneezing where the virus is contained in the secretions. Some droplets fall onto surfaces where they can survive for up to days on materials such as stainless steel or plastics, while others remain airborne as fine aerosols that may be inhaled through the mouth or nose and be infectious for up to 3 hours.

Mitigation approaches have caused entire economies to shut down with physical distancing between people being required to inhibit the spread. Interior air in tightly sealed buildings appears to exacerbate the spread as the virus can propagate and infect people in areas where air circulation or fans aid in aerosol dispersal. To reduce the concentration of infectious aerosols in conditioned buildings, the American Society of Heating, Refrigerating and Air-Conditioning Engineers (ASHRAE) recommends (a) increasing outdoor air ventilation by opening intake air dampers to 100%, (b) enhancing filtration over code minimums (e.g. HEPA filters), (c) keeping systems running longer (24/7 if possible), and (d) bypassing energy recovery ventilation systems. However, these recommendations, if applied, can significantly increase energy usage worldwide. The estimated increase in energy needed to condition additional make up air is greater than 5 times over current use. Thus, there remains a need to perform high confidence sterilization of indoor air with low power requirements and with minimum impact to existing building infrastructures.

SUMMARY

Devices, methods and techniques are disclosed for high confidence sterilization of indoor air with low power requirements. These mitigation techniques can be beneficial for combating airborne viruses and may also be generally applicable to sterilization of contaminants in an enclosure, such as a room or a section of a room, as well as multiple rooms, sections of a building and the entire interior of a building.

In one example aspect, an apparatus for deactivating pathogen carried in droplets includes a power source, an energy storage coupled to the power source and configured to store electric charges, a set of electrodes arranged in a specified geometry to have a fixed characteristic impedance, and a switch positioned between the energy storage and the set of electrodes. The switch is configured to operate to establish a pulsed electric field on the set of electrodes. When the switch is in a closed position, the energy storage is configured to supply the electric charges to the set of electrodes such that the electric field applied on the set of electrodes is higher than a threshold. When the switch is in an open position, the set of electrodes is configured to return the electric charges to the energy storage according to the fixed characteristic impedance.

In another example aspect, a method for deactivating pathogen carried in airborne droplets includes drawing, by an air suction component of a sterilization device, surrounding air from an external environment into the sterilization device; and directing the air to a set of electrodes that is connected to an energy storage via a switch of the sterilization device. The energy storage is configured to store electric charges, and the set of electrodes is arranged in a specified geometry to have a fixed characteristic impedance. The method includes operating the switch to establish a pulsed electric field on the set of electrodes, which includes applying, via the energy storage, an electric field that is higher than a threshold to the set of electrodes when the switch is in a closed position, and returning electric charges to the energy storage according to the fixed characteristic impedance of the set of electrodes when the switch is in an open position. The method also includes directing the air that has passed through the set of electrodes to the external environment.

In another example aspect, a method for deactivating pathogen carried in droplets on a material includes inserting the material through an opening formed by a first segment and a second segment of a sterilization device. The first segment includes a first group of electrodes and the second segment includes a second group of electrodes. The electrodes are connected to an energy storage via a switch of the sterilization device. The energy storage is configured to store electric charges, and the electrodes are arranged in a specified geometry to have a fixed characteristic impedance. The method includes operating the switch to establish a pulsed electric field on the electrodes, which includes applying, via the energy storage, an electric field that is higher than a threshold to the electrodes when the switch is in a closed position, and returning electric charges to the energy storage according to the fixed characteristic impedance of the electrodes when the switch is in an open position. The method also includes moving the material across the opening while operating the switch.

The above and other aspects and features of the disclosed technology are described in greater detail in the drawings, the description and the claims.

BRIEF DESCRIPTION OF THE DRAWINGS

FIG. 11 is a flowchart representation of a method for deactivating pathogen carried in droplets on a material in accordance with one or more embodiments of the present technology.

DETAILED DESCRIPTION

Airborne pathogens such as bacteria, fungi and viruses spread disease leading to illness, loss of life, and economic disruption. The recent COVID-19 pandemic has proven to be particularly devastating and appears to spread primarily through aerosol droplets in indoor settings. A nonthermal method to deactivate the virus and other pathogens in building air can greatly decrease spread of disease and the associated health and economic damage.

Multiple techniques have been developed to disinfect air, such as electrostatic fields, ionic purifiers, and dielectric barrier discharge. Table 1 shows some of the existing pathogen sterilization methods for fluid and air.

TABLE 1

Example Pathogen Sterilization Methods

| No. | Name | Method | Species |
|---|---|---|---|
| 1 | Mizuno | Pulsed Electric Field with transport fluid | Swine Vesicular Disease Virus |
| 2 | Mizuno | Pulsed Electric Field with transport fluid | Equine Herpesvirus-1 |
| 3 | Vaze | Dielectric Barrier Discharge for 0.25 min, 100% exposure | E. Coli |
| 4 | Vaze | Ozone only | E. Coli |

TABLE 1-continued

Example Pathogen Sterilization Methods

| No. | Name | Method | Species |
|---|---|---|---|
| 5 | Vaze | Dielectric Barrier Discharge for 0.25 min, 75% exposure | E. Coli |
| 6 | Gallagher | Dielectric Barrier Discharge, 100% particles in system cycled through in 10 s | E. Coli |
| 7 | Pastuszka | Electron wind generator | Bacteria |
| 8 | Pastuszka | Electron wind generator | Fungi |
| 9 | Yao | Electrostatic at 15 kV/cm | P. fluorescens bacteria |
| 10 | Huang | Filter only | B. subtilis |
| 11 | Huang | Filter enhanced with ions | B. subtilis |
| 12 | Huang | Filter only | E. coli |
| 13 | Huang | Filter enhanced with ions | E. coli |
| 14 | Huang | Filter only | A. versicolor |
| 15 | Huang | Filter enhanced with ions | A. versicolor |
| 16 | Huang | Filter only | A. niger |
| 17 | Huang | Filter enhanced with ions | A. niger |
| 18 | Huang | Filter only | H11N9 |
| 19 | Huang | Filter enhanced with ions | H11N9 |
| 20 | McDevitt | Various UV-C at 15 J/m² at 50% relative humidity | Influenza virus (A/PR/8/34 H1N1) |

Figure 1A:
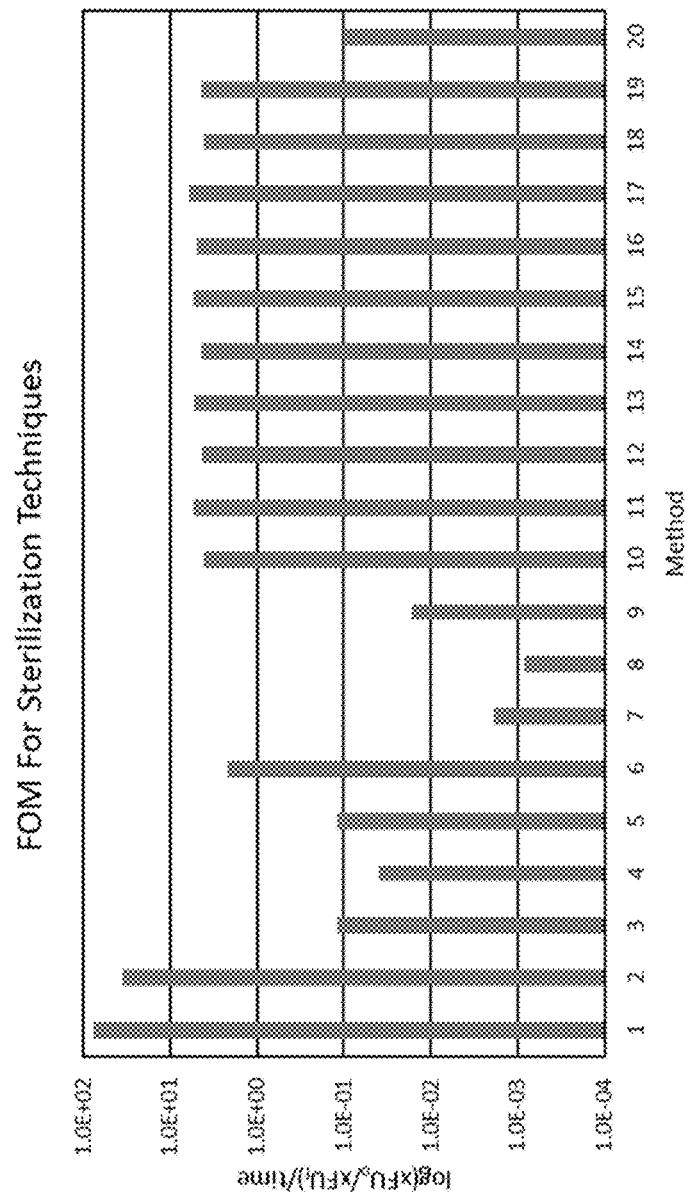
FIG. 1A illustrates an example chart showing a figure of merit (FOM) of some of the conventional sterilization methods.
Figure 1B:
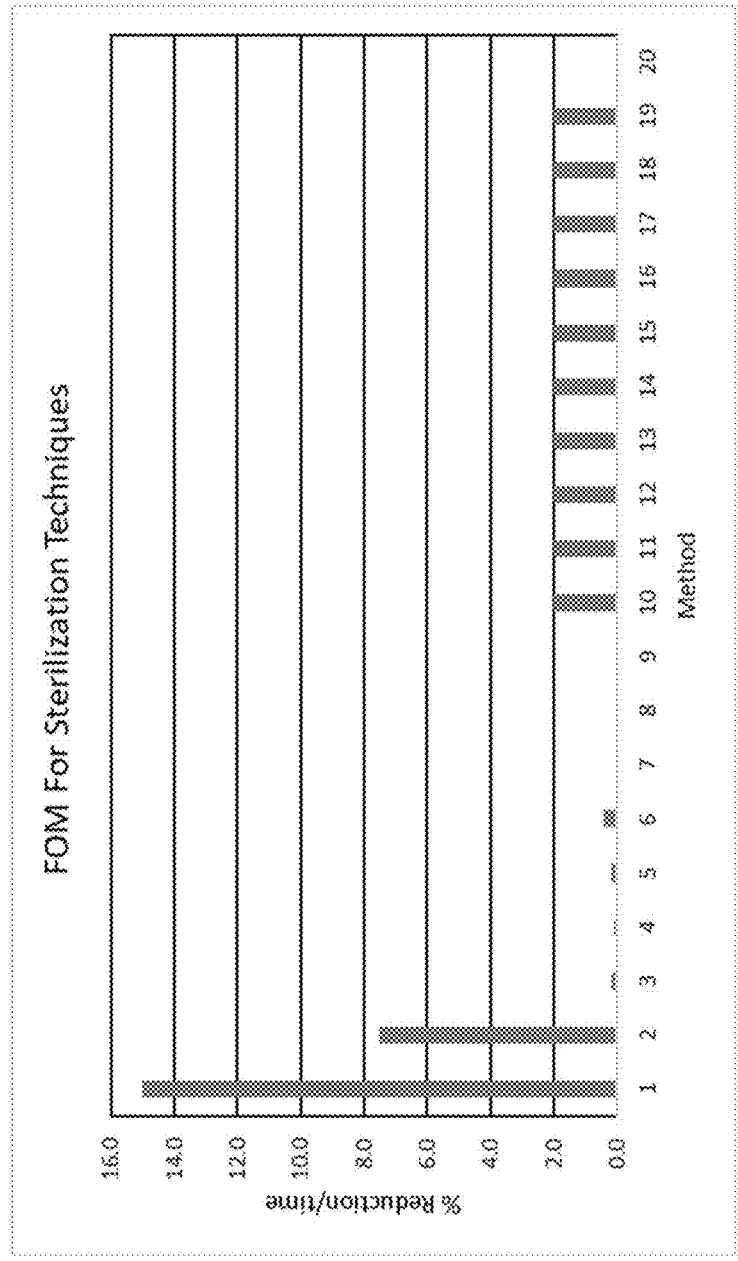
FIG. 1B illustrates an example chart showing percentages of reduction per unit time associated with some of the conventional sterilization methods.

FIG. 1A illustrates an example chart 100 showing a figure of merit (FOM) of the sterilization methods listed in Table 1. The FOM is estimated by taking the $\log_{10}$ of the reduction in colony or plaque forming units divided by the time required to achieve the reduction. FIG. 1B illustrates an example chart 150 showing percentage of reduction per unit of time of the sterilization methods listed in Table 1.

Mizuno (methods 1 and 2) used a non-thermal, pulsed electric field for fluid sterilization. The pulsed electric field was generated by discharging an 850-pF capacitor charged to 30 kV (~0.4 J/pulse) into a flow cell. Care was taken not to affect the virus with temperature rise. The pulse width was determined by the conductivity of the fluid carrying the virus (from 0.5 to 500 µs) with the dielectric relaxation ($\tau=\rho\varepsilon$) ranging from 0.5 ns to 0.2 µs. It is noted that the relaxation time for human saliva to be between ≈5-500 ns. Swine Vesicular Disease and Equine Herpesvirus were studied respectively. Deactivation ratios of the virus were $10^4$ to $>10^5$. Electron microscope analysis of the virus after subjection to the pulsed treatment showed that the RNA within the core collapsed. Effectiveness was attributed to the electric field, not the power dissipated in the dielectric fluid as deactivation occurred over a wide range of conductivity of the transport fluid at low temperature.

This phenomenon observed by Mizuno is consistent with later findings by Zhou that observed the collapse of DNA molecules above an externally applied critical electric field that suggested the cause for the collapse as a polarization of ions beyond the Debye and Oosawa-Manning condensed layer. Presumably, the quasi-neutral RNA polyanion and surrounding elements in a virus are perturbed by the external field leading to molecular rearrangement and destruction. Zhou also showed the ability to manipulate the shape of the DNA molecule in TBE buffer (>90% water) starting at 200 V/cm.

Vaze and Gallagher (methods 3-6) used a high-power plasma barrier discharge to expose airborne E. Coli directly to the discharge. FOM varied from −0.45 for ozone treatment alone to 4.6 with the dielectric barrier discharge. Vaze used a pulsed plasma driven by 28 kV and 50 A; Gallagher similarly used a pulsed source of similar properties, but reported on using a 600 µs pulse. No tests were performed on viruses. Pastuszka (methods 7 and 8) reported on a commercial electrostatic wind generator. The device required recirculation multiple times and eventually achieved a reduced level of pathogens (bacteria and fungi, respectively). FOM was −1.9 for bacteria and −2.3 for fungi in approximately 6 hours. No data was reported on the effect of viruses. Yao (method 9) used an electrostatic field to deactivate bacteria. Fields up to 15 kV/cm were used. An FOM of −0.78 was calculated for this approach.

Huang (methods 10-19) used unipolar ions to enhance standard heating and ventilation filters. Several species were studied that included bacteria, fungi, and viruses. Air movement was approximately 1.1 m/s through a 20 mm thick standard ventilation filter. Sampling was done immediately past the ion emitter-filter combination. The large FOM (5.7 to 6.5) is attributed to the short time the pathogen traverses the filter and is trapped. The percentage of pathogens trapped, however, is low and ranged from 75-90% for bacteria and fungi and about 40% for the virus studied. The degree of deactivation of the pathogen trapped in the filter was not studied.

Finally, McDevitt (method 20) studied the deactivation effects of UV-C on influenza virus up to an energy flux of 15 J/m2 at 50% relative humidity. The reduction in the survival of the virus was observed to be approximately 50, but the effectiveness changed from −200% to +25% for a range of relative humidity of 25% to 75%. The nominal FOM is estimated to be approximately 2.2.

As compared to the airborne methods (methods 3-20), the Mizuno data in FIG. 1 is striking in that the degree of deactivation of the virus by directly attacking the viral RNA is a factor of $10^4$ to $>10^5$. However, it is noted that the Mizuno data is for electrodes separated by the transport fluid—there was no air gap between the electrode and the liquid suspending the virus. In air stream containing water droplets, application of Mizuno becomes unclear.

This patent document discloses techniques related to systems and methods of applying high electric fields to an air stream to disrupt viral DNA/RNA and structures in cellular pathogens, thereby rendering them inactive. The disclosed techniques can provide, among other features and benefits, a high confidence method to reduce infectious units by a ratio of greater than $10^4$. Because the techniques rely on electric field strength, current draw can be minimal, and the system can use little electrical energy. The disclosed techniques can be implemented as a system that is easily added onto existing building air handling systems or deployed as room or personal devices. The disclosed techniques can also be implemented as a device to perform high confidence sterilization of surfaces and materials.

It is noted that RNA and similar molecules are net charged molecules or polyanions. Some prior systems discuss the external effects of this and the natural shielding or quasi-neutrality that occurs, where the equilibrium can be upset with an external electric field. These molecules and viruses also have a polarization property in an electric field that can be characterized by a net permittivity. For the case of DNA and viruses, a relative permittivity increase can occur over vacuum of approximately $\varepsilon_r \approx 8$ as an upper limit. From this value, for a virus suspension in water with no air gap between the electrodes and water, it is possible to estimate the electric field within the virus. For simplicity, the virus structures are treated as spherical. Thus, the critical electric field required to cause collapse for RNA indicate a field of approximately twice that of the applied electric field within the RNA/DNA structure, or approximately 60 kV/cm.

For viruses contained in large water droplets with airgaps in between, applying electric fields to the virus particle itself sufficient to destroy the virus becomes problematic. A water droplet with $\varepsilon_r \approx 80$ has a tendency to become polarized and shield the interior from the high externally applied electric field. Breakdown of air at atmospheric pressure—which can limit the electric field strengths—is approximately 30 kV/cm. However, that limit can be significantly exceeded with short pulses. For instance, it has been demonstrated that fields as high as 160 kV/cm can be achieved in a 200 µm gap for seven nanoseconds before electrical breakdown occurs. But even these extremely high electric field levels applied to the water droplets suspended in air are insufficient to observe the pathogen destroying effects demonstrated by Mizuno. Thus, it can be concluded that for virus materials contained in water droplets suspended in air, it is very difficult to achieve the electric field required to deactivate the virus by collapsing the DNA or RNA. Thus, it is necessary to free as much water surrounding the virus as possible.

When subjected to an electric field, a water droplet becomes nearly instantaneously polarized giving rise to mechanical deformation and sometimes jet formation at the apex. For example, submicron droplets down to 30 nm can be caused by a similar process. A spherical droplet enhances the electric field at the apex which can also generate corona discharge. Further deformation under the influence of the electric field causes an increase in the field enhancement. A stability criterion for a water droplet in an electric field has been established. When the tangent angle is approximately $\pi/2$ at the waist (near spherical) and the field is greater than 11 kV/cm, the droplet is naturally unstable giving rise to further atomization. Droplets that are thin in the direction of the electric field require a higher electric field for instability and presumably those thinner at the waist require lower electric field to be unstable. Enhancement at the tips of an elongated structure, however, can have a tendency to realign the structure to the electric field forming more favorable conditions. The SARS-CoV-2 virus is 60-140 nm and near spherical, whereas the *Escherichia coli* bacteria is about 2 µm in length and about 0.5 µm at the waist. Additionally, measured the dielectric constant of cellular structures are expected to be between 2.6 and 4.9. Given such virus dimensions, an electric field can be used to shed the water surrounding a pathogen. Once the water is shed, a sufficiently high electric field can be applied to cause DNA/RNA collapse in the case of a virus, or permeation of the cell or nucleus wall in the case of a cell type pathogen without causing air breakdown. Thus, a pulsed electric field of sufficient intensity can be used to sterilize an air flow. Additionally, depending on electrode shape, the pulsed electric field can be used to sterilize surfaces or materials. In particular, it is noted that the FOM of the Mizuno data was limited by the technology used to generate the 30 Hz pulses. Higher repetition rate can significantly raise the FOM by $\log_{10}$ of the increase in rate.

Figure 2:
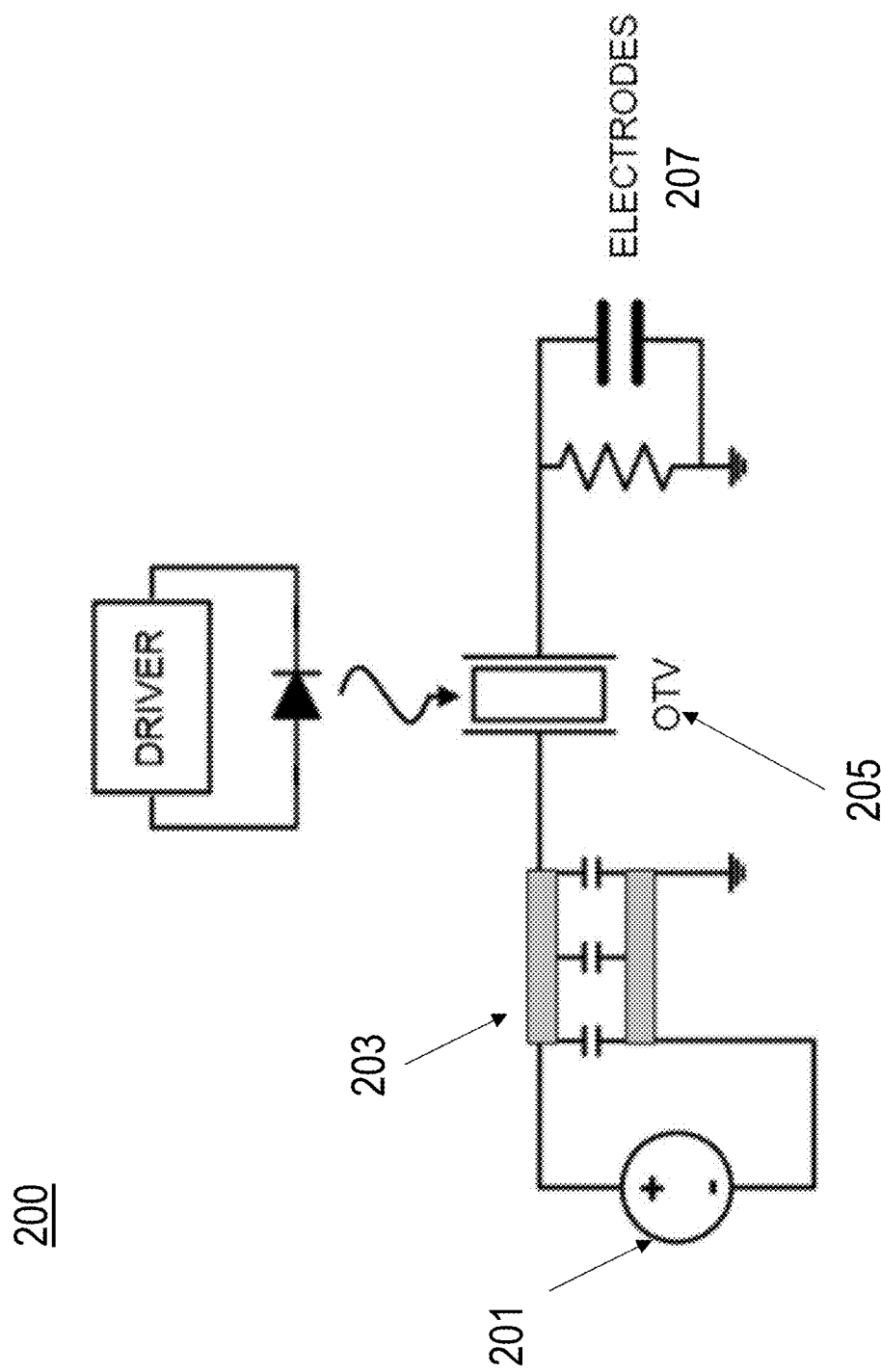
FIG. 2 illustrates an example configuration of an air sanitization apparatus using high-voltage pulses in accordance with one or more embodiments of the present technology.
Figure 3:
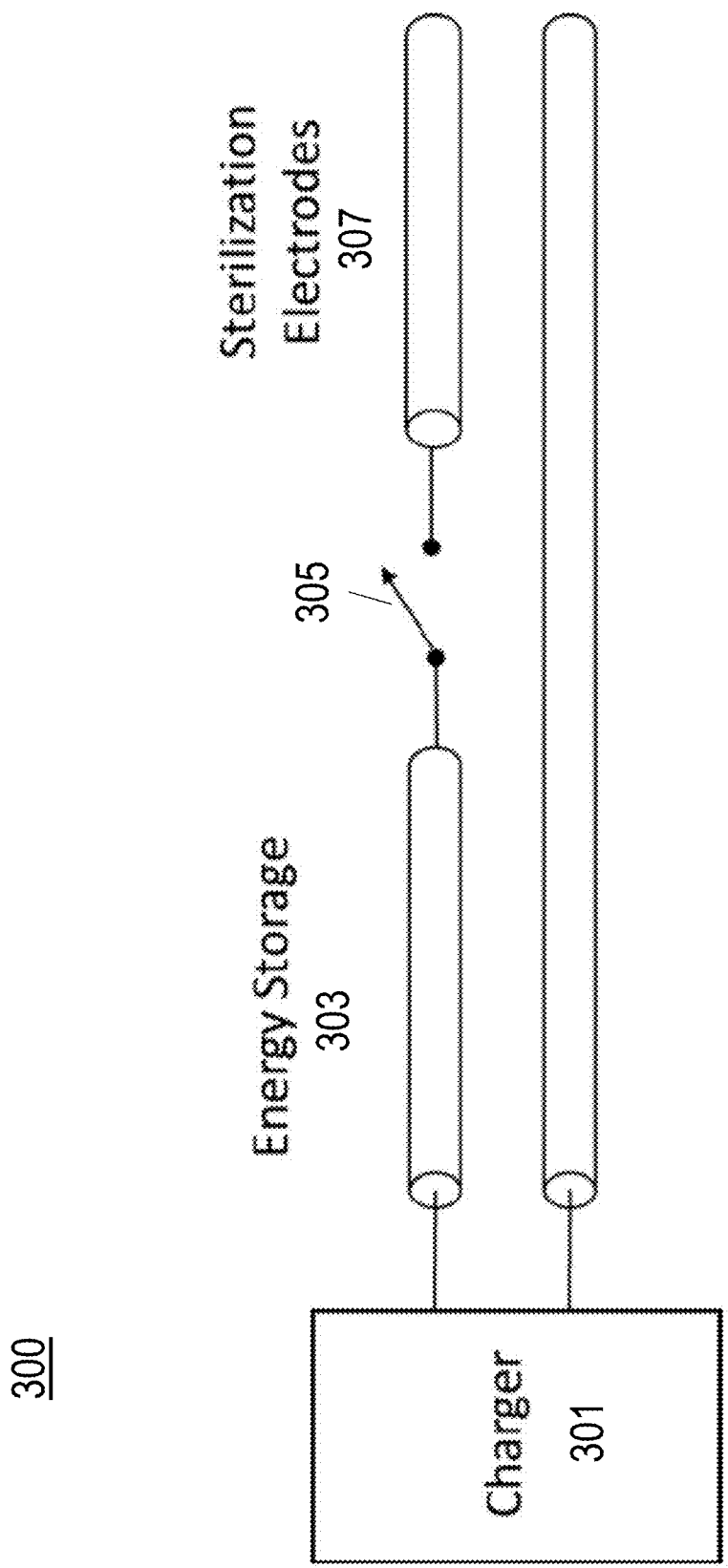
FIG. 3 illustrates an example configuration of energy recovery in a sanitization apparatus in accordance with one or more embodiments of the present technology.
Figure 4:
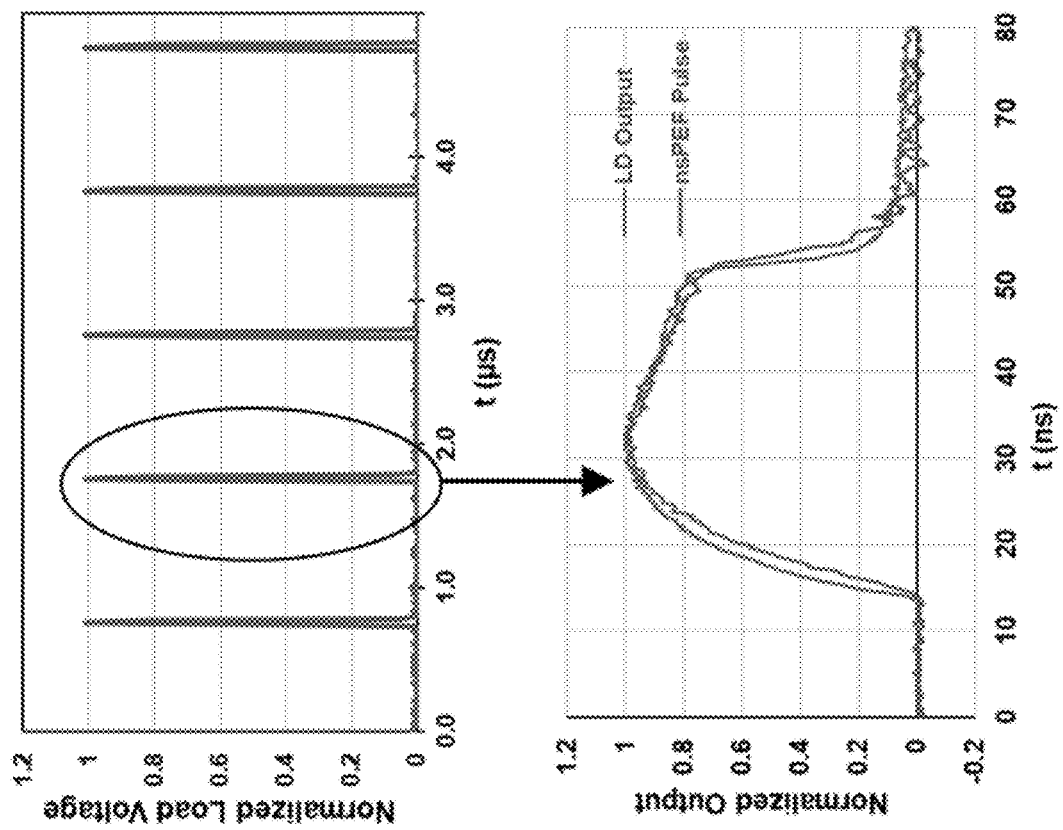
FIG. 4 illustrates an example high-voltage pulse formation in accordance with one or more embodiments of the present technology.
Figure 5:
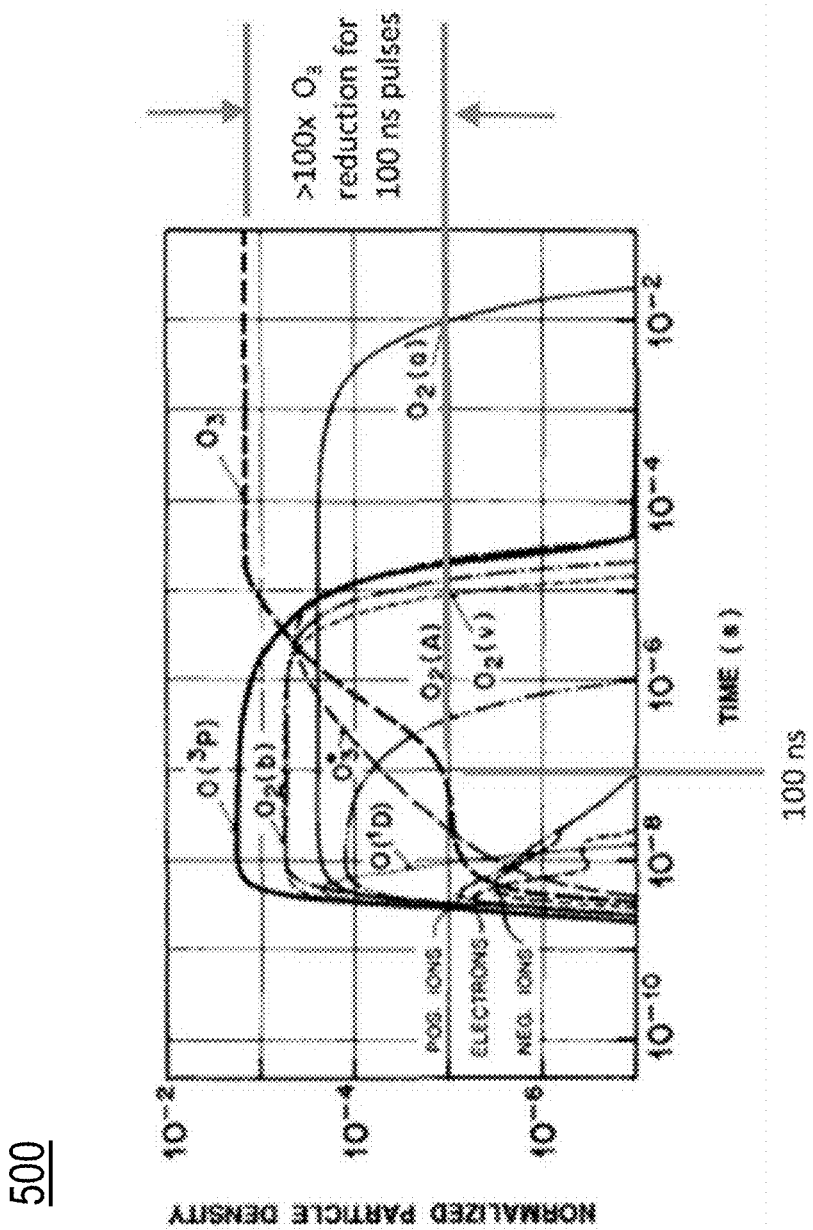
FIG. 5 illustrates an example chart showing additional benefits of using short pulses in accordance with one or more embodiments of the present technology.

FIG. 2 illustrates an example configuration 200 of an air sanitization apparatus using high-voltage pulses in accordance with one or more embodiments of the present technology. The configuration 200 includes a power source 201, an energy storage 203, a switch 205, and a set of electrodes 207. The energy storage 203 (e.g., a charged transmission line) is coupled to the power source and configured to store electric charges. The energy storage 203 can also include a capacitor, an inductor, a combination of the two, or devices like batteries and similar elements. The electric field is established on a set of electrodes 207 and is used for sterilization of pathogens. The set of electrodes 207 is arranged in a specified geometry to have a fixed characteristic impedance to provide a "lossless" line so that all of the energy (except some nominal losses) can be fed back into the energy storage 203. The switch 205 is positioned between the energy storage and the set of electrodes. The switch is configured to operate to establish a pulsed electric field on the set of electrodes 207. In some embodiments, the switch 205 is configured to operate at a rate of applying at least 10 pulses from an electrode pair to the airstream to ensure a high probability of sterilization. In some embodiments, the frequency is higher than 5000 Hz to establish a pulsed electric field on the set of electrodes. For example, for a commercial building, flow speeds can be as high as 1000 ft/min requiring a high voltage pulse repetition frequency greater than:

$$\frac{\text{Air flow speed}}{\text{Action distance of Electrodes}} \times \text{pulse required} \qquad \text{Eq. (1)}$$

In some embodiments, the switch 205 can be an optical switch, such as a light-driven optical transconductance varistor (OTV) 301 as high voltage solid state switches start to become inefficient above 5000 Hz and certainly above 10,000 Hz. The OTV is a device that is made of wide bandgap materials and controlled by light. The OTV is capable of very high pulse repetition rate (e.g., greater than 5000 Hz), short duration (e.g., 10's ns), and switching of many 10's of kV. The OTV also allows bi-directional current flow. Additional details of the OTV are described in U.S. Pat. No. 9,142,339, the content of which is incorporated by reference as part of the disclosure. When the energy is delivered in a short pulse to establish the pulsed electric field on the electrodes 307, the energy is contained capacitively and/or inductively in the electrodes 307 and the majority of the energy is fed back again into the storage element 303 that delivered the energy. The process is first to charge up the energy storage element 303, then close the switch 305 and allow that energy to build up in the electrodes 307. This process depletes the energy in the storage element so that the energy in the electrodes can be returned to the storage element again. At this point the switch 305 is opened to contain the energy in the storage element. The process can be repeated at a high rate (e.g., from 5000 Hz to above 1 MHz).

As discussed above, to minimize energy use, the electrodes are arranged in a specified geometry to have a fixed characteristic impedance to provide a "lossless" line so that almost all the energy can be fed back into the energy storage. FIG. 3 illustrates an example configuration 300 of energy recovery in a sanitization apparatus in accordance with one or more embodiments of the present technology. The configuration 300 includes a power source 301 (e.g., a charger) that replaces energy used during a cycle, an energy storage 303 (e.g., a capacitor), a switch 305, and sterilization electrodes 307. The storage element 303 and the electrodes 307 form two transmission lines of equal impedance separated by the switch 305. When the pulse is required at the electrodes 307, the switch 305 becomes conducting until the storage transmission line is fully discharged. At that point, the switch 305 becomes non-conducting to maintain the voltage on the electrodes 307. To end the pulse on the electrodes 307, the switch 305 closes once again, but reopens once the energy from the electrodes 307 is recovered.

It is noted that two conductors (e.g., one carrying a forward current and the other a return current) with some specified geometry can exhibit a fixed electrical property based on the geometry alone (e.g., "characteristic impedance"). That is, the characteristic impedance is fixed and does not depend on the angular frequency that is defined as the ratio of the voltage and current of a pure sinusoidal wave of the same frequency travelling along the line. For example, parallel rods can be used as transmission lines as shown in FIG. 2 to provide the desired geometry. When the pulsed source sees the impedance, it delivers energy as if the impedance was a simple resistor. At the same time, guided electromagnetic wave is injected into the electrode at the speed of light. When this wave sees the open at the other end of the electrode, the wave reflects in the exact backward direction back toward the pulsed source. Because the pulsed source is provided out of an equivalent characteristic impedance structure of an identical electrical length, all of the energy (except some nominal losses) can be fed back into the storage electrical line.

To enable low-energy usage, low duty cycle ultra-fast pulses can be used. The ultra-fast pulses allow the energy recovery scheme that takes advantage of the combined inductive and capacitive effects of the electrodes, leading to near total energy recovery. In some embodiments, using transmission lines as the energy storage 303 can be optimal for recovering the energy. However, other storage elements (e.g., a capacitor, an inductor, a combination thereof etc.) can also be used. FIG. 4 illustrates an example high-voltage pulse formation 400 in accordance with one or more embodiments of the present technology. The upper part of FIG. 4 shows example formation of pulses that have a cycle of shorter than 1 μs. The lower part of FIG. 4 shows the corresponding normalized voltage output in one particular cycle.

FIG. 5 illustrates an example chart 500 showing additional benefits of using short pulses in accordance with one or more embodiments of the present technology. Ozone, which is toxic above 0.1 ppm, is produced by electric fields and discharges in air. Many of the conventional air disinfection processes produce ozone that is released into the atmosphere. As illustrated in FIG. 5, for a given electric field, ozone production can be reduced by over 100× by using pulses shorter than 100 ns. Because ultra-fast pulses have a cycle width of 10's of ns, ozone production can be kept to a minimum and meet regulatory requirements. In some embodiments, ozone formation using the ultra-fast pulses is 100× lower than using direct current.

FIG. 6 shows a schematic diagram 600 showing an end-view of a set of electrodes and an air flow in accordance with one or more embodiments of the present technology. As shown in FIG. 6, air flow 601 is directed through electrodes 603 configured to minimize the level of electric field enhancements needed to achieve breakdown. A quasi-static electric field meeting a first set of criteria (e.g., the stability criterion for a water droplet) can be applied to the first set of electrodes 603*a* in order to atomize larger droplets into smaller ones that are approximately the size of the pathogen. The remaining electrodes 603*b* apply an electric field in the remainder of the region according to a set second of criteria that can deactivate the pathogen. For example, an electric field that is above 10 kV/cm can be applied to break down bacteria and viruses.

In some embodiments, an electric field that satisfies both sets of criteria can be applied to the same set of electrodes 603 to achieve breakdown and deactivation of the pathogen. For example, Mizuno used 60 pulses at 30 Hz to realize a reduction in the viable virus count of $10^4$-$10^5$. A building air velocity through a filter is estimated to vary around 140 ft/min. At this rate, a volume of air takes $6\times10^{-4}$ s to travel a typical filter thickness of 1". Producing a high repetition rate (e.g., from 5000 Hz to above 1 MHz) using, for example, switching electronics, approximately 600-700 pulses can be applied to an airstream in the path length of a standard air filter, achieving an FOM of $5.2\times10^5$, a factor of nearly $10^4$ greater than any other methods described in Table 1. Further, the atomization and sterilization effects are electric field dependent, thus a close array of electrodes can be used at lower voltages to make a device consumer safe. If made compact enough, the close array of electrodes can be inserted into respirators for personal protection equipment.

Figure 6:
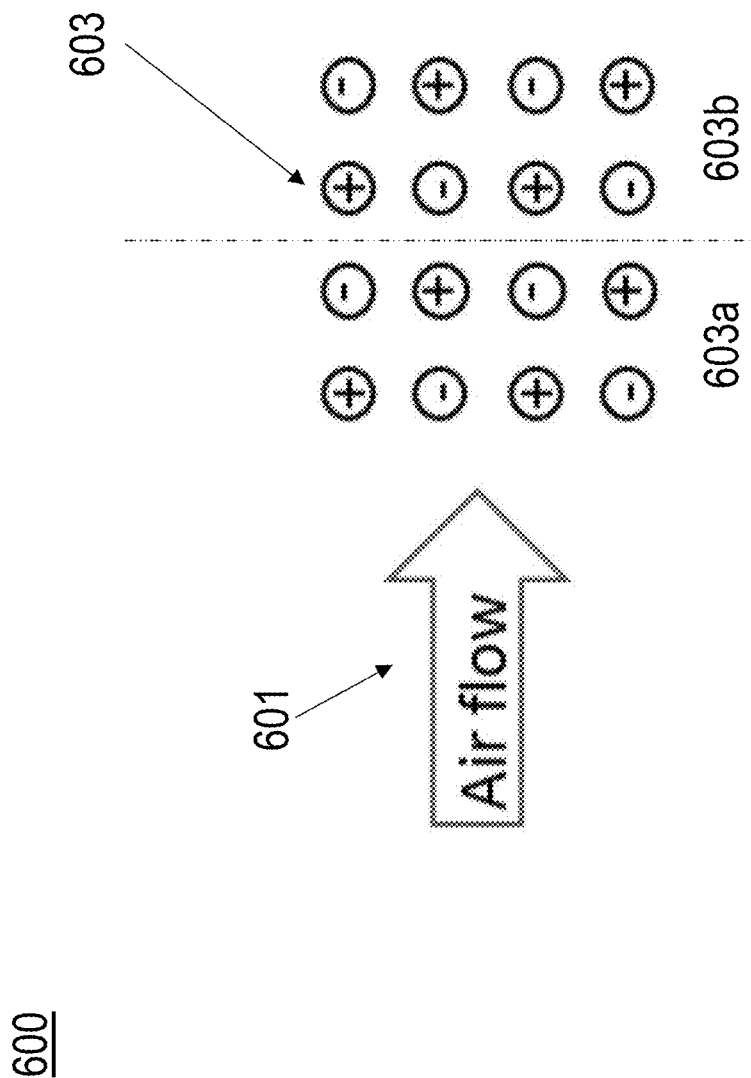
FIG. 6 shows a schematic diagram showing an end-view of a set of electrodes and an air flow in accordance with one or more embodiments of the present technology.
Figure 7:
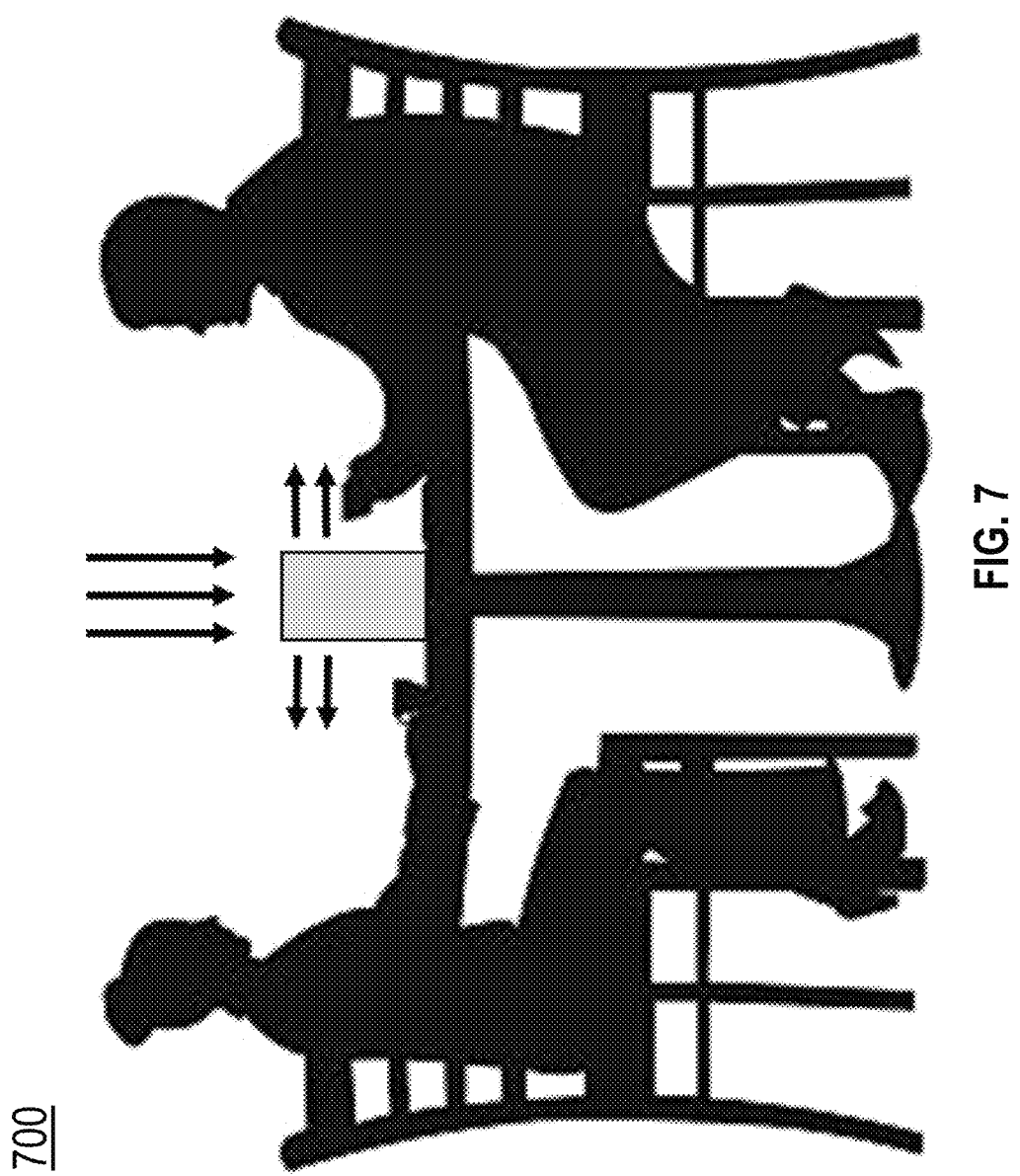
FIG. 7 illustrates a side view of an example implementation of an air sanitization apparatus in accordance with one or more embodiments of the present technology.

FIG. 7 illustrates an example air sanitization apparatus 700 in accordance with one or more embodiments of the present technology. As shown in FIG. 7, the apparatus includes a suction device (e.g., an electric air pump) and omnidirectional sterilized air exhaust configuration positioned within an enclosure. In this particular example, the suction device is configured to draw air downwards from above via one or more openings. The suction device can also be configured to draw air from alternative directions. The air is directed to the omnidirectional sterilized air exhaust configuration (e.g., as shown in FIG. 6). The omnidirectional sterilized air exhaust configuration is configured to sterilize the air by applying ultra-fast pulses to break down the water droplets carrying the virus and to deactivate the virus. The sterilized air is then directed towards the environment via one or more conduits or pipes of the air sanitization apparatus. As one example applicating, using the apparatus as depicted in FIG. 7, higher densities in various venues can be allowed during a pandemic outbreak without the requirement of social distancing, which is used such that individuals are required to maintain significant distances (typically 2 m) from each other to prevent transmission via shed virus in exhaled breath.

Figure 8A:
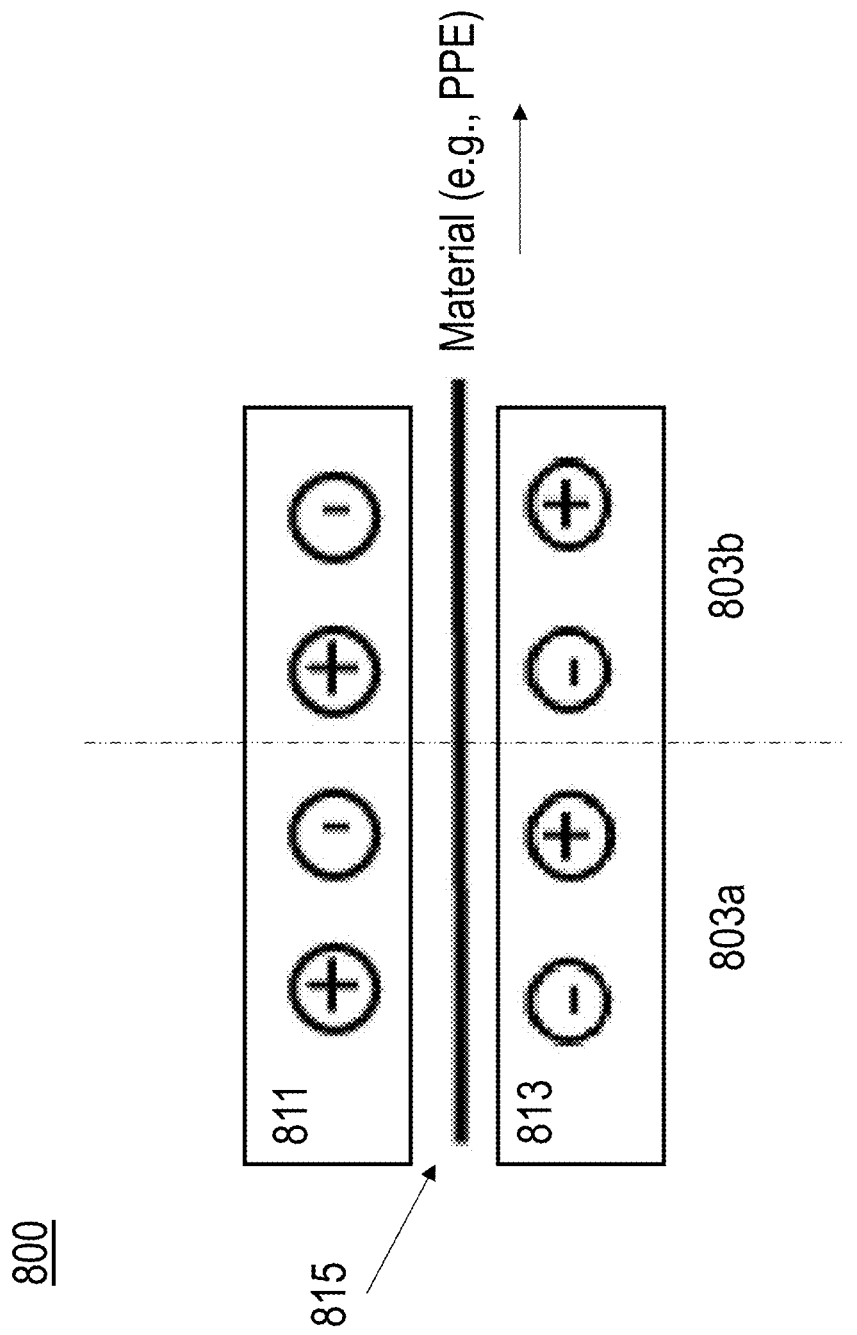
FIG. 8A illustrates a side view of an example surface sterilization apparatus in accordance with one or more embodiments of the present technology.

FIG. 8A illustrates an example surface sterilization apparatus 800 in accordance with one or more embodiments of the present technology. In this example, the electrodes are arranged into two groups positioned in separate flat segments 811, 813 forming an opening 815. The flat segments 811, 813 can be substantially parallel to each other (e.g., the degree between the two segments is in a range of −5 to 5 degrees). The material to be sterilized can be inserted between the two segments 811, 813 that includes the electrodes via the opening 815. Each of the electrodes can have a round cross-sectional shape or any other shapes so long as the electric field enhancements are properly mitigated. In the particular example shown in FIG. 8A, a Personal Protection Equipment (PPE) material can be inserted between the electrodes from left to right. In some embodiments, the surface first passes through a first set of electrodes 803a to which a first electric field is applied to atomize larger droplets into smaller ones that are approximately the size of the pathogen. The surface then passes through a second set of electrodes 803b with a second electric field. The water surrounding the pathogen is minimized to allow the second electric field to more readily penetrate to deactivate the pathogen and sterilize the material. Alternatively, an electric field that satisfies both criteria—the stability criterion for breaking down a water droplet and the criterion for deactivating the pathogen—can be applied to the electrodes to sterilize the material. For example, as discussed above, a near spherical water droplet can break down when the electric field is greater than 11 kV/cm (the stability criterion). A pathogen of *P. fluorescens* bacteria is inactivated when the field of 15 kV/cm is applied for a predetermined duration (the criterion for deactivating the pathogen). Therefore, an electric field that is higher than 15 kV/cm can satisfy both criteria to breakdown the droplets and deactivate the pathogen.

Figure 8B:
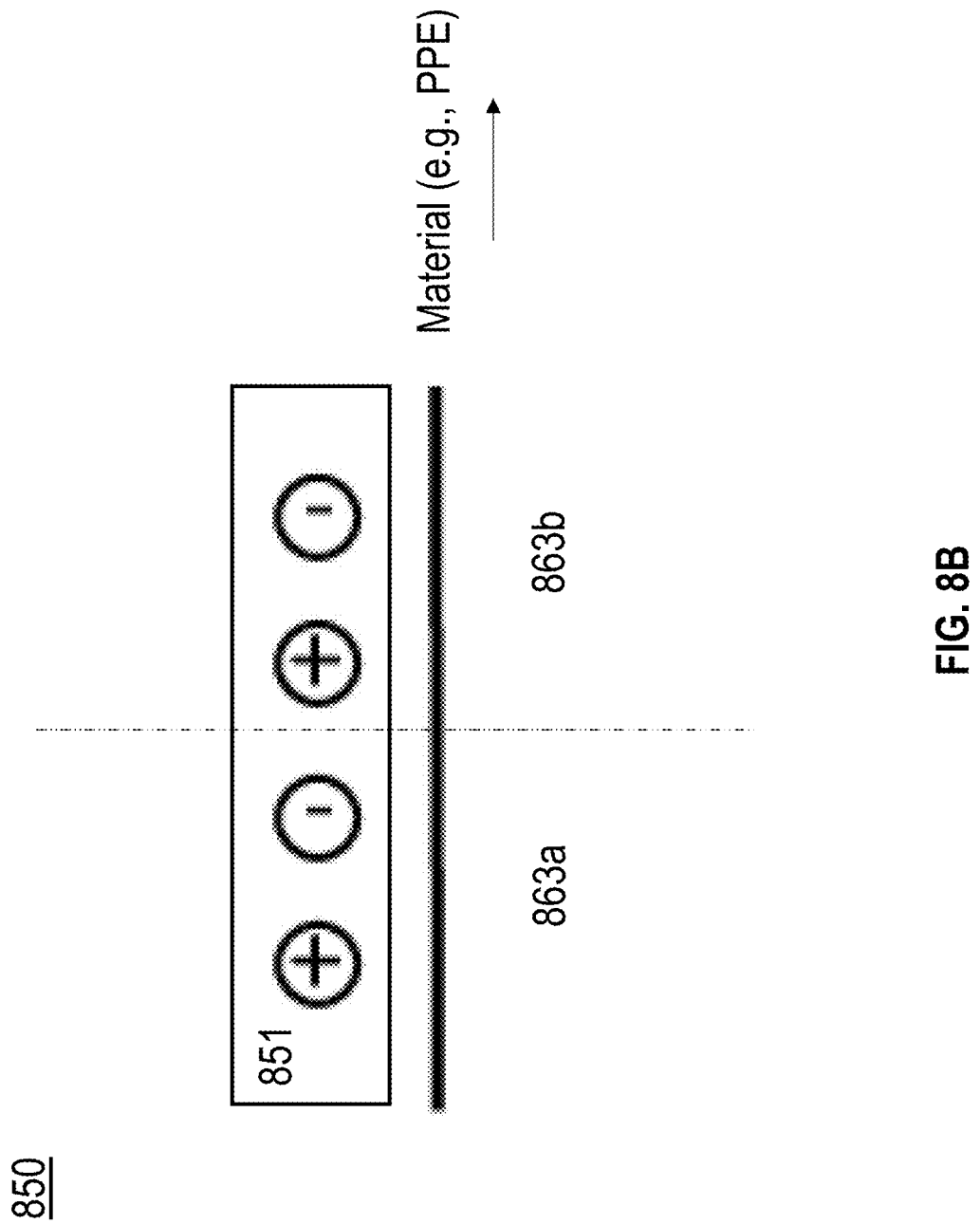
FIG. 8B illustrates a side view of another example surface sterilization apparatus in accordance with one or more embodiments of the present technology.

In some embodiments, depending on the material and accessibility to an opposing surface, the device can be built non-symmetrically, e.g., either using 811 or 813 by itself without the opposing electrode set. FIG. 8B illustrates an example surface sterilization apparatus 850 in accordance with one or more embodiments of the present technology. In this example, a single flat segment 851 is used. As the PPE material passes through the electrodes 863a and 863b, one or more electric fields that satisfy the criteria can be applied to the electrodes to sterilize the material.

Figure 9:
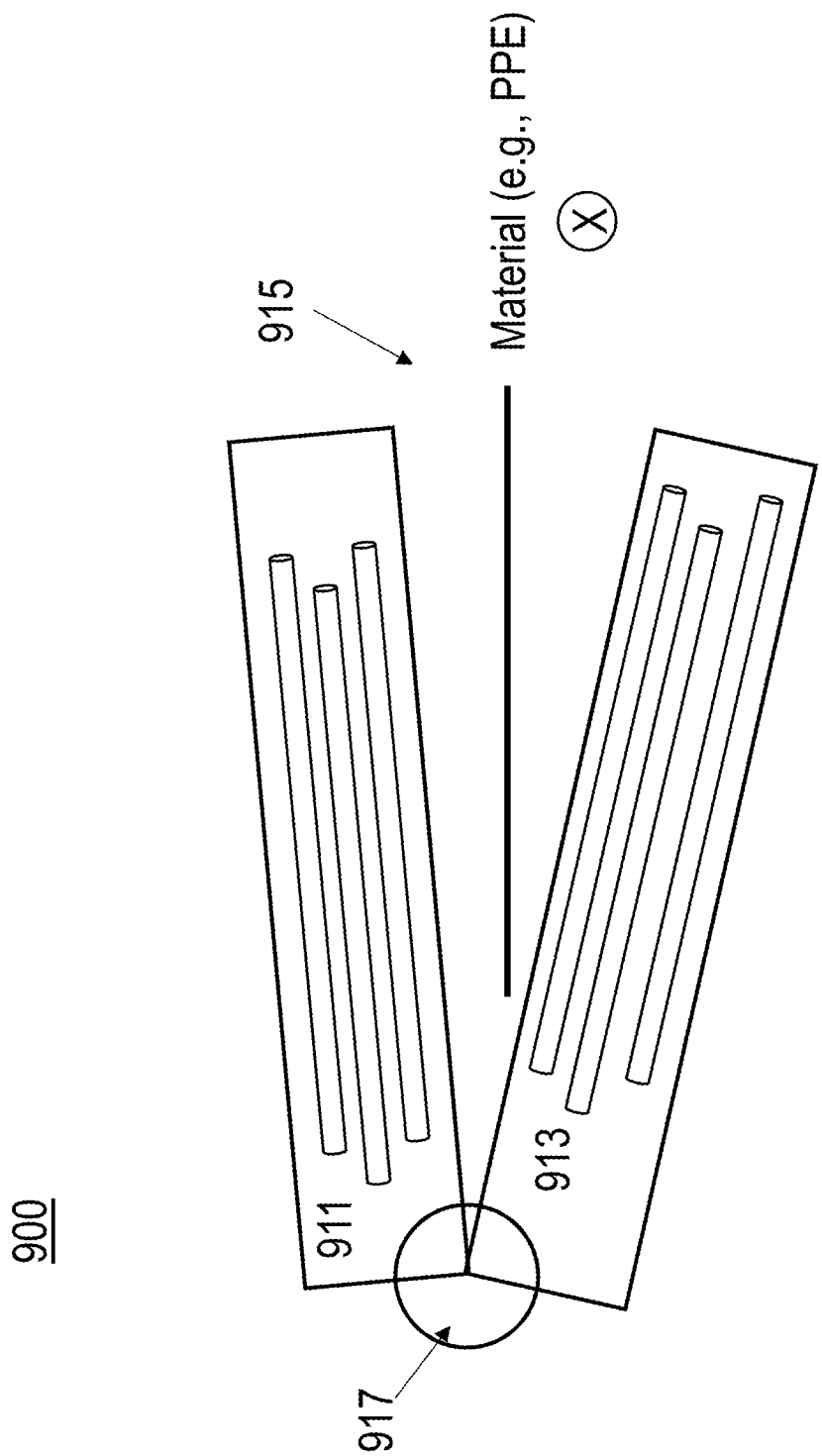
FIG. 9 illustrates a side view of yet another example surface sterilization apparatus in accordance with one or more embodiments of the present technology.

FIG. 9 illustrates another example surface sterilization apparatus 900 in accordance with one or more embodiments of the present technology. In this example, the flat segments 911, 913 are connected by a hinge 917 to enable adjustment of the opening 915. The electrodes are arranged into groups, each positioned in the respective segment. The electrodes can have a round cross-section or any other shapes to properly mitigate the electric field enhancements. The material to be sterilized can be inserted in the opening 915 and move across the electrodes. For example, as shown in FIG. 9, the PPE material moves in the direction into the plane of the paper. An electric field that satisfies both criteria—the stability criterion for breaking down a water droplet and the criterion for deactivating the pathogen—can be applied to the electrodes to sterilize the material.

In one example aspect, an apparatus for deactivating pathogens carried in droplets is disclosed. The apparatus includes a power source, an energy storage coupled to the power source and configured to store electric charge, a set of electrodes arranged in a specified geometry to have a fixed characteristic impedance, and a switch positioned between the energy storage and the set of electrodes. The switch is configured to operate to establish a pulsed electric field on the set of electrodes for deactivating pathogens carried in droplets. The energy storage is configured to supply the electric charges to the set of electrodes such that the electric field established on the set of electrodes is higher than a threshold, and the set of electrodes is configured to return the electric charges to the energy storage according to the fixed characteristic impedance.

In some embodiments, the threshold is determined based on (1) a first threshold that is sufficient to break down the droplets and (2) a second threshold that is sufficient to deactivate the pathogen carried in the droplets that have broken down. In some embodiments, the switch is configured to operate at a rate that is higher than 5000 Hz to establish the pulsed electric field on the set of electrodes. In some embodiments, the switch is configured to allow bidirectional current flows to enable the electric charges to return to the energy storage when the switch is in the open position. In some embodiments, the switch comprises an optical switch. In some embodiments, the optical switch is an optical transconductance varistor.

In some embodiments, each of the set of electrodes includes a plurality of electrodes that are arranged parallel with respect to one another, each electrode having a round cross section. In some embodiments, the energy storage and the set of electrodes form two transmission lines of equal impedance separated by the switch. The switch is configured to be conducting until the energy storage is fully discharged to establish the electric field on the set of electrodes and to be non-conducting to maintain a voltage on the set of electrodes. In some embodiments, the switch is configured to be conducting to enable the set of electrodes to return the electric charges to the energy storage.

In some embodiments, the apparatus is positioned in an air supply duct of a building. In some embodiments, the apparatus further includes an enclosure that encloses the energy storage, the set of electrodes, and the switch. The apparatus includes an air pump positioned within the enclosure. The air pump is coupled to the power source to draw surrounding air into the enclosure via one or more openings of the enclosure and supply the drawn air to the set of electrodes. The apparatus also includes one or more conduits configured to direct air after passing through the set of electrodes to an external environment.

In some embodiments, the set of electrodes is divided into a first group of electrodes and a second group of electrodes. The apparatus includes a first segment that encloses the first group of electrodes and a second segment that encloses the second group of electrodes. The first segment and the second segment form an opening to allow a material that carries the droplets to pass therethrough. In some embodiments, the first segment and the second segment are substantially parallel to each other. In some embodiments, the apparatus further includes a hinge coupled to the first segment and the second segment such that the opening formed by the first segment and the second segment is adjustable to allow the material to pass through.

Figure 10:
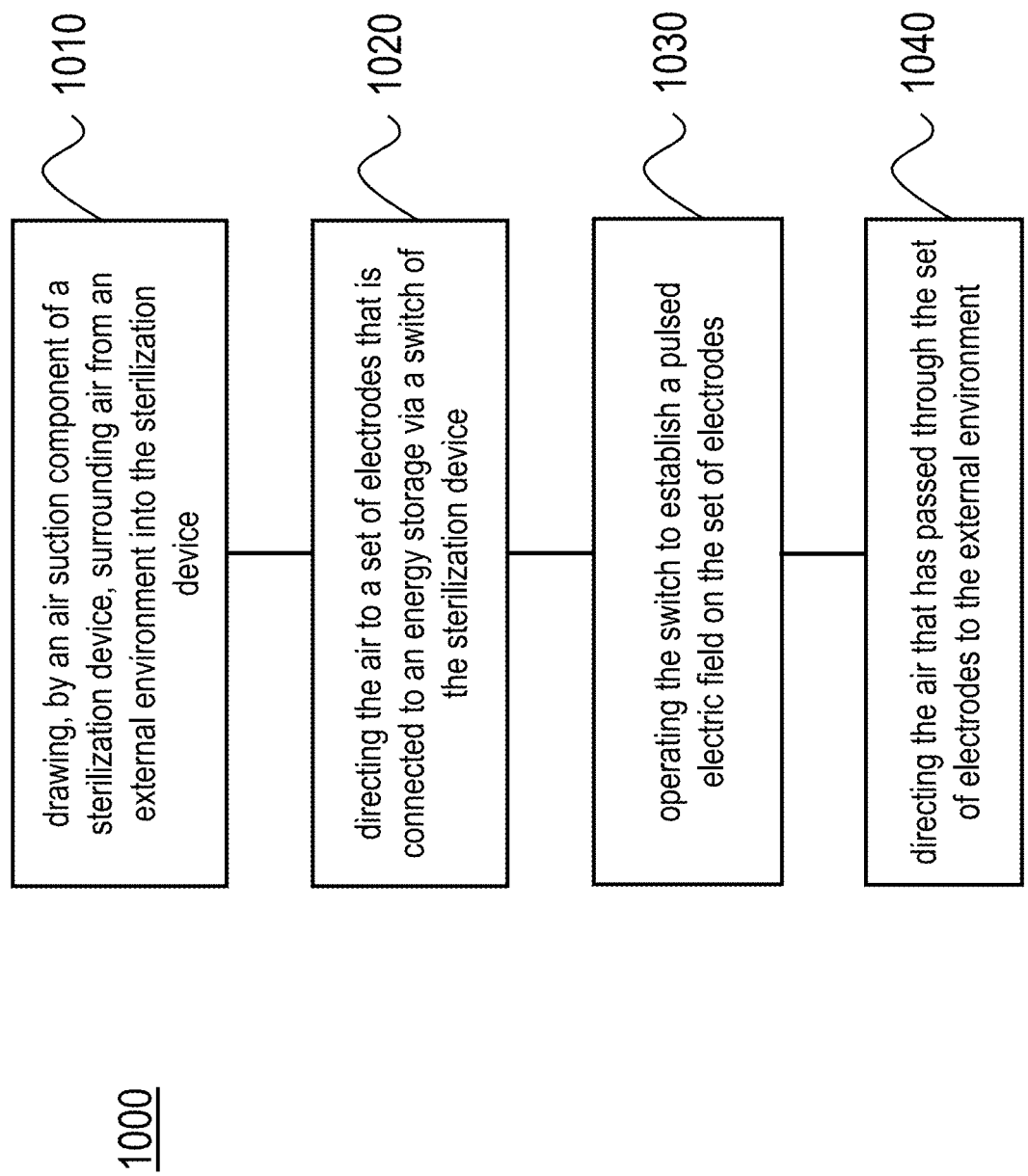
FIG. 10 is a flowchart representation of a method for deactivating pathogen carried in airborne droplets in accordance with one or more embodiments of the present technology.

FIG. 10 is a flowchart representation of a method 1000 for deactivating pathogen carried in airborne droplets in accordance with one or more embodiments of the present technology. The method 1000 includes, at operation 1010, drawing, by an air suction component of a sterilization device, surrounding air from an external environment into the sterilization device. The method 1000 includes, at operation 1020, directing the air to a set of electrodes that is connected to an energy storage via a switch of the sterilization device. The energy storage is configured to store electric charges, and the set of electrodes is arranged in a specified geometry to have a fixed characteristic impedance. The method 1000 includes, at operation 1030, operating the switch to establish a pulsed electric field on the set of electrodes. Operating the switching includes establishing, using the energy storage, an electric field that is higher than a threshold to the set of electrodes, and returning the electric charges to the energy storage according to the fixed characteristic impedance of the set of electrodes. The method 1000 also includes, at operation 1040, directing the air that has passed through the set of electrodes to the external environment.

In some embodiments, the threshold is determined based on (1) a first threshold sufficient to break down the droplets and (2) a second threshold sufficient to deactivate the pathogen carried in the droplets that have been broken down. In some embodiments, operating the switch includes operating the switch at a rate that is higher than 5000 Hz to establish the pulsed electric field on the set of electrodes. In some embodiments, the switch is configured to allow bidirectional current flows to enable the electric charges to return to the energy storage when the switch is in the open position. In some embodiments, the switch comprises an optical switch. In some embodiments, the optical switch is an optical transconductance varistor.

In some embodiments, each of the set of electrodes includes a plurality of electrodes that are arranged parallel with respect to one another, each electrode having a round cross section. In some embodiments, the energy storage and the set of electrodes form two transmission lines of equal impedance separated by the switch. The operating of the switch includes operating the switch as a conducting element until the energy storage is fully discharged to establish the electric field on the set of electrodes and operating the switch as a non-conducting element to maintain a voltage on the set of electrodes. In some embodiments, the operating of the switch further includes operating the switch as a conducting element to enable the set of electrodes to return the electric charges to the energy storage.

FIG. 11 is a flowchart representation of a method 1100 for deactivating pathogen carried in droplets on a material in accordance with one or more embodiments of the present technology. The method 1100 includes, at operation 1110, inserting the material through an opening formed by a first segment and a second segment of a sterilization device. The first segment includes a first group of electrodes and the second segment includes a second group of electrodes. The electrodes are connected to an energy storage via a switch of the sterilization device. The energy storage is configured to store electric charges, and the electrodes are arranged in a specified geometry to have a fixed characteristic impedance. The method 1100 includes, at operation 1120, operating the switch to establish a pulsed electric field on the electrodes, which includes stablishing, via the energy storage, an electric field that is higher than a threshold to the electrodes, and returning the electric charges to the energy storage according to the fixed characteristic impedance of the electrodes. The method 1100 also includes, at operation 1130, moving the material across the opening while operating the switch.

In some embodiments, the threshold is determined based on (1) a first threshold sufficient to atomize the droplets and (2) a second threshold sufficient to deactivate the pathogen carried in the droplets that have been broken down. In some embodiments, operating the switch includes operating the switch at a rate that is higher than 5000 Hz to establish the pulsed electric field on the set of electrodes. In some embodiments, the switch is configured to allow bidirectional current flows to enable the electric charges to return to the energy storage when the switch is in the open position. In some embodiments, the switch comprises an optical switch. In some embodiments, the optical switch is an optical transconductance varistor.

In some embodiments, each of the set of electrodes includes a plurality of electrodes that are arranged parallel with respect to one another, each electrode having a round cross section. In some embodiments, the energy storage and the set of electrodes form two transmission lines of equal impedance separated by the switch. The operating of the switch includes operating the switch as a conducting element until the energy storage is fully discharged to establish the electric field on the set of electrodes and operating the switch as a non-conducting element to maintain a voltage on the set of electrodes. In some embodiments, the operating of the switch further includes operating the switch as a conducting element to enable the set of electrodes to return the electric charges to the energy storage.

As demonstrated in the discussions above, most of the conventional airborne techniques create ozone, are low confidence and cannot easily be retrofitted into air handling systems that recirculate air throughout a building. The techniques disclosed herein provide an experimentally proven, non-thermal technique utilizing a very prompt pulsed electric field that can effectively kill or deactivate airborne pathogens (both virial and cellular) thus providing high-throughput, high-confidence airstream disinfection. Because the disclosed techniques are based on an electric field and not dependent on a conduction current between electrodes, the power requirement is extremely low. Furthermore, the system introduces a minimal backpressure on the airflow thus causing minimal pressure drop and consequent loss of efficiency. Using the disclosed techniques, a significant reduction ($>10^4$) of colony or plaque forming units in the airflow can be achieved in a single pass.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. An apparatus for deactivating pathogens carried in droplets, comprising:
   a power source;
   an energy storage coupled to the power source and configured to store electric charges;
   a set of electrodes arranged in a specified geometry to have a fixed characteristic impedance that allows energy to be fed back into the energy storage; and
   a switch positioned between the energy storage and the set of electrodes, wherein the switch is configured to establish a pulsed electric field on the set of electrodes for deactivating the pathogens carried in droplets,
   wherein the energy storage is configured to supply the electric charges to the set of electrodes such that the pulsed electric field established on the set of electrodes is higher than a threshold, and
   wherein the set of electrodes is configured to return the electric charges to the energy storage according to the fixed characteristic impedance,
   wherein the set of electrodes is divided into a first group of electrodes and a second group of electrodes, the apparatus further comprising:
   a first segment that encloses the first group of electrodes; and
   a second segment that encloses the second group of electrodes, wherein the first segment and the second segment form an opening to allow a material that carries the droplets to pass therethrough.

2. The apparatus of claim 1, wherein the switch is configured to operate at a rate that is higher than 5000 Hz to establish the pulsed electric field on the set of electrodes.

3. The apparatus of claim 1, wherein the switch is configured to allow bidirectional current flows to enable the electric charges to return to the energy storage when the switch is in an open position.

4. The apparatus of claim 1, wherein the switch comprises an optical switch.

5. The apparatus of claim 4, wherein the optical switch is an optical transconductance varistor.

6. The apparatus of claim 1, wherein each of the set of electrodes includes a plurality of electrodes that are arranged parallel with respect to one another, each electrode having a round cross section.

7. The apparatus of claim 1, wherein the energy storage and the set of electrodes form two transmission lines of equal impedance separated by the switch, wherein the switch is configured to be conducting until the energy storage is fully discharged to establish the pulsed electric field on the set of electrodes and to be non-conducting to maintain a voltage on the set of electrodes.

8. The apparatus of claim 7, wherein the switch is configured to be conducting to enable the set of electrodes to return the electric charges to the energy storage.

9. The apparatus of claim 1, wherein the apparatus is positioned in an air supply duct of a building.

10. The apparatus of claim 1, further comprising:
    an enclosure that encloses the energy storage, the set of electrodes, and the switch;
    an air pump positioned within the enclosure, wherein the air pump is coupled to the power source to draw surrounding air into the enclosure via one or more openings of the enclosure and supply the drawn air to the set of electrodes; and
    one or more conduits configured to direct air after passing through the set of electrodes to an external environment.

11. The apparatus of claim 1, wherein the first segment and the second segment are substantially parallel to each other.

12. The apparatus of claim 1, further comprising:
    a hinge coupled to the first segment and the second segment such that the opening formed by the first segment and the second segment is adjustable to allow the material to pass through.

13. A method for deactivating pathogen carried in airborne droplets, comprising:
    drawing, by an air suction component of a sterilization device, surrounding air from an external environment into the sterilization device;
    directing the drawn air to a set of electrodes that is coupled to an energy storage via a switch of the sterilization device, wherein the energy storage is configured to store electric charges, and wherein the set of electrodes is arranged in a specified geometry to have a fixed characteristic impedance that allows energy to be fed back into the energy storage, wherein the set of electrodes is divided into a first group of electrodes and a second group of electrodes;
    operating the switch to establish a pulsed electric field on the set of electrodes, the operating comprising:
       establishing, using the energy storage, an electric field that is higher than a threshold to the set of electrodes, and
       returning the electric charges to the energy storage according to the fixed characteristic impedance of the set of electrodes; and
    directing air that has passed through the set of electrodes to the external environment wherein the sterilization device further comprises a first segment that encloses the first group of electrodes and a second segment that encloses the second group of electrodes, wherein the first segment and the second segment form an opening to allow the air to pass therethrough.

14. The method of claim 13, wherein the threshold is determined based on (1) a first threshold sufficient to atomize the airborne droplets and (2) a second threshold sufficient to deactivate the pathogen carried in the airborne droplets that have been broken down.

15. The method of claim 13, wherein operating the switch comprises:
   operating the switch at a rate that is higher than 5000 Hz to establish the pulsed electric field on the set of electrodes.

16. The method of claim 13, wherein the switch is configured to allow bidirectional current flows to enable the electric charges to return to the energy storage when the switch is in an open position.

17. The method of claim 13, wherein the switch comprises an optical switch.

18. The method of claim 17, wherein the optical switch is an optical transconductance varistor.

19. The method of claim 13, wherein each of the set of electrodes includes a plurality of electrodes that are arranged parallel with respect to one another, each electrode having a round cross section.

20. The method of claim 13, wherein the energy storage and the set of electrodes form two transmission lines of equal impedance separated by the switch, wherein the operating of the switch comprises:
   operating the switch as a conducting element until the energy storage is fully discharged to establish the electric field on the set of electrodes, and
   operating the switch as a non-conducting element to maintain a voltage on the set of electrodes.

21. The method of claim 20, wherein the operating of the switch further comprises:
   operating the switch as a conducting element to enable the set of electrodes to return the electric charges to the energy storage.

22. A method for deactivating pathogen carried in droplets on a material, comprising:
   inserting the material through an opening formed by a first segment and a second segment of a sterilization device, wherein a set of electrodes of the sterilization device is divided into a first group of electrodes and a second group of electrodes, and wherein the first segment encloses the first group of electrodes and the second segment encloses the second group of electrodes to allow the material that carries the droplets to pass therethrough, wherein the set of electrodes is connected to an energy storage via a switch of the sterilization device, wherein the energy storage is configured to store electric charges, and wherein the set of electrodes are arranged in a specified geometry to have a fixed characteristic impedance that allows energy to be fed back into the energy storage;
   operating the switch to establish a pulsed electric field on the set of electrodes, the operating comprising:
      establishing, via the energy storage, an electric field that is higher than a threshold to the set of electrodes, and
      returning the electric charges to the energy storage according to the fixed characteristic impedance of the set of electrodes; and
   moving the material across the opening while operating the switch.

23. The method of claim 22, wherein the threshold is determined based on (1) a first threshold sufficient to atomize the droplets and (2) a second threshold sufficient to deactivate the pathogen carried in the droplets that have been broken down.

24. The method of claim 22, wherein operating the switch comprises:
   operating the switch at a rate that is higher than 5000 Hz to establish the pulsed electric field on the set of electrodes.

25. The method of claim 22, wherein the switch is configured to allow bidirectional current flows to enable the electric charges to return to the energy storage when the switch is in an open position.

26. The method of claim 22, wherein the switch comprises an optical switch.

27. The method of claim 26, wherein the optical switch is an optical transconductance varistor.

28. The method of claim 22, wherein each of the set of electrodes includes a plurality of electrodes that are arranged parallel with respect to one another, each electrode having a round cross section.

29. The method of claim 22, wherein the energy storage and the set of electrodes form two transmission lines of equal impedance separated by the switch, wherein the operating of the switch comprises:
   operating the switch as a conducting element until the energy storage is fully discharged to establish the electric field on the set of electrodes, and
   operating the switch as a non-conducting element to maintain a voltage on the set of electrodes.

30. The method of claim 29, wherein the operating of the switch further comprises:
   operating the switch as a conducting element to enable the set of electrodes to return the electric charges to the energy storage.

* * * * *